United States Patent
Crews et al.

(10) Patent No.: US 12,343,004 B2
(45) Date of Patent: *Jul. 1, 2025

(54) SURGICAL TOOLS WITH OCCLUDED BLADE

(71) Applicant: CILAG GMBH INTERNATIONAL, Zug (CH)

(72) Inventors: Andrew Crews, Cincinnati, OH (US); Michael Chirumbolo, Cincinnati, OH (US); John A. Hibner, Mason, OH (US); Rudolph H. Nobis, Mason, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 37 days.

This patent is subject to a terminal disclaimer.

(21) Appl. No.: 18/230,939

(22) Filed: Aug. 7, 2023

(65) Prior Publication Data

US 2023/0371942 A1    Nov. 23, 2023

Related U.S. Application Data

(63) Continuation of application No. 17/079,603, filed on Oct. 26, 2020, now Pat. No. 11,717,282, which is a
(Continued)

(51) Int. Cl.
*A61B 17/04* (2006.01)
*A61B 17/062* (2006.01)
(Continued)

(52) U.S. Cl.
CPC ...... *A61B 17/0467* (2013.01); *A61B 17/0469* (2013.01); *A61B 17/0483* (2013.01);
(Continued)

(58) Field of Classification Search
CPC ............ A61B 17/0467; A61B 17/0469; A61B 17/0483; A61B 17/062; A61B 17/29;
(Continued)

(56) References Cited

U.S. PATENT DOCUMENTS 5,342,381 A * 8/1994 Tidemand .......... A61B 18/1445
606/174
5,665,100 A    9/1997 Yoon
(Continued)

FOREIGN PATENT DOCUMENTS

EP    0913126 A2    5/1999
JP    S5886152 A    5/1983
(Continued)

OTHER PUBLICATIONS

International Search Report and Written Opinion, received for PCT Application No. PCT/IB2018/057467, mailed on Jan. 7, 2019, 18 pages.

*Primary Examiner* — Robert A Lynch
(74) *Attorney, Agent, or Firm* — Joshua D. Young

(57) ABSTRACT

Surgical tools that are capable of both manipulating a needle and cutting surgical thread during a suturing operation can sometimes be problematic due to inadvertent severing of the surgical thread. Surgical tools capable of exposing a bladed cutting surface only when severing of surgical thread is desired can substantially alleviate this issue. Such surgical tools may comprise an end effector comprising an end effector axle, a first jaw and a second jaw rotatably mounted to the end effector axle, and a first cutting body having a first blade and second cutting body having a second blade. The first cutting body is configured to move in tandem with the first jaw and the second cutting body is configured to move
(Continued)

in tandem with the second jaw, such that the first and second blades are occluded when the first and second jaws are closed or partially opened.

11 Claims, 14 Drawing Sheets

Related U.S. Application Data continuation of application No. 15/725,508, filed on Oct. 5, 2017, now Pat. No. 10,820,898.

(51) Int. Cl.
| | | |
|---|---|---|
| *A61B 17/29* | (2006.01) | |
| *A61B 17/295* | (2006.01) | |
| *A61B 17/3201* | (2006.01) | |
| *A61B 34/00* | (2016.01) | |
| *A61B 34/30* | (2016.01) | |

(52) U.S. Cl.
CPC .......... *A61B 17/062* (2013.01); *A61B 17/295* (2013.01); *A61B 2017/047* (2013.01); *A61B 2017/2941* (2013.01); *A61B 2017/2947* (2013.01); *A61B 17/3201* (2013.01); *A61B 34/30* (2016.02); *A61B 2034/305* (2016.02); *A61B 34/71* (2016.02)

(58) Field of Classification Search
CPC .............. A61B 17/295; A61B 17/3201; A61B 2017/00353; A61B 2017/047; A61B 2017/2926; A61B 2017/2941; A61B 2017/2947; A61B 34/30; A61B 34/71; A61B 2034/305; A61B 18/1442; A61B 18/1445; A61B 2018/1452

See application file for complete search history.

(56) References Cited

U.S. PATENT DOCUMENTS

| | | | |
|---|---|---|---|
| 5,984,939 | A | 11/1999 | Yoon |
| 6,024,744 | A * | 2/2000 | Kese .................. A61B 18/1445 |
| | | | 606/45 |
| 8,831,782 | B2 | 9/2014 | Itkowitz |
| 9,999,431 | B2 | 6/2018 | Shelton, IV et al. |
| 10,820,898 | B2 * | 11/2020 | Crews ................. A61B 17/295 |
| 11,717,282 | B2 * | 8/2023 | Crews ................ A61B 17/0467 |
| | | | 606/174 |
| 2001/0037712 | A1 | 11/2001 | Furuhata et al. |
| 2007/0156172 | A1 | 7/2007 | Alvarado |
| 2007/0244515 | A1 * | 10/2007 | Fanous ................ A61B 17/295 |
| | | | 606/174 |
| 2010/0042140 | A1 | 2/2010 | Cunningham |
| 2015/0025549 | A1 | 1/2015 | Kilroy et al. |
| 2015/0209965 | A1 | 7/2015 | Low et al. |
| 2015/0313676 | A1 | 11/2015 | Deodhar |
| 2016/0058460 | A1 | 3/2016 | Ohki |
| 2016/0287252 | A1 | 10/2016 | Parihar |
| 2018/0000543 | A1 | 1/2018 | Hibner |
| 2019/0105032 | A1 | 4/2019 | Crews et al. |

FOREIGN PATENT DOCUMENTS

| | | |
|---|---|---|
| JP | H10179602 A | 7/1998 |
| JP | 2007319294 A | 12/2007 |
| WO | 2014151621 A1 | 9/2014 |
| WO | 2014151952 A1 | 9/2014 |
| WO | 2017042791 A2 | 3/2017 |

* cited by examiner

SURGICAL TOOLS WITH OCCLUDED BLADE

CROSS-REFERENCE TO RELATED APPLICATIONS

This application is a continuation of U.S. Patent App. Pub. No. 2021/0038215, entitled "Surgical Tools with Occluded Blade" filed Oct. 26, 2020, which is a continuation of U.S. Pat. No. 10,820,898, entitled "Surgical Tools with Occluded Blade" filed Oct. 5, 2017, the contents of which are hereby incorporated in their entirety.

BACKGROUND

Minimally invasive surgical (MIS) tools and procedures can often be preferred over traditional open surgical techniques due to their ability to decrease post-operative recovery time and to leave minimal scarring. Laparoscopic surgery is one type of MIS procedure in which one or more small incisions are formed in the abdomen of a patient and a trocar is inserted through each incision to provide a surgical access pathway for an appropriate surgical tool. Trocars can additionally provide an internal seal assembly for maintaining insufflation of the abdomen during a surgical procedure.

A variety of MIS tools can be inserted into the abdominal cavity of a patient via a trocar and maneuvered from outside the abdomen. Laparoscopic surgical tools, for example, are often similar to those used in traditional surgical procedures, with the exception that laparoscopic surgical tools possess an elongate shaft extending from an end effector to a location outside the abdomen. The end effector is the surgically functional part of the surgical tool. The elongate shaft protrudes externally through a trocar when the surgical tool is inserted in the abdomen of a patient, and an external portion of the surgical tool provides a means for manipulating and communicating with the end effector. Once inserted in a patient's body, the end effector can engage and/or treat tissue in a number of ways to achieve a desired diagnostic or therapeutic effect. Illustrative end effectors of laparoscopic and similar surgical tools include, for example, scissors, graspers, needle drivers, clamps, staplers, cauterizers, suction tools, irrigation tools, and clip-appliers.

Robotic surgery represents a specialized class of laparoscopic surgical procedures. Instead of directly engaging a surgical tool as in traditional laparoscopic surgery, a surgeon instead manipulates and engages the surgical tool using an electronic interface communicatively coupled to a robotic manipulator. Manipulation and engagement of a surgical tool under robotic control can allow much more precise surgical procedures to be performed in many instances. A surgeon need not necessarily even be in the operating room with the patient. Advantageously, robotic surgical systems can allow intuitive hand movements to be realized by maintaining a natural eye-hand axis. In addition, robotic surgical systems can incorporate a "wrist" coupling the end effector to the elongate shaft to provide natural, hand-like articulation during a robotic surgical procedure. The wrist can also facilitate an expanded and more complex range of motion than is possible with a human wrist, which can allow highly elaborate and precise surgical procedures to be performed.

Many laparoscopic and robotic surgical procedures utilize an end effector that is capable of performing a suturing operation. As in conventional surgical procedures, laparoscopic and robotic suturing operations utilize a needle attached to a length of surgical thread for placing one or more sutures in a tissue. Laparoscopic and robotic suturing operations utilize a needle driver as the end effector for manipulating the needle when placing sutures. The needle driver comprises opposing jaws that articulate between closed and open positions when grasping and releasing the suturing needle. Upon completion of a suturing operation, the surgical thread must be severed (cut) to remove the needle and excess surgical thread from the patient.

Bladed cutting instruments such as surgical scissors or shears are commonly used to sever surgical thread during surgical procedures. In laparoscopic and robotic surgical procedures, such cutting instruments can be included on the same surgical tool as a needle driver but may also form part of a separate surgical tool. Both approaches can be problematic. Introducing a separate surgical tool into a patient to sever surgical thread may increase the time and cost of conducting a procedure due to use of an additional tool. In addition, the separate surgical tool may require insertion of an additional trocar, which can increase patient trauma and prolong recovery times. In contrast, conventional surgical tools incorporating both a needle driver and a bladed cutting instrument may run the risk of inadvertently and prematurely severing the surgical thread before a suturing operation is complete. This risk may represent an unacceptable obstacle for adoption of multi-function surgical tools for some users.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure generally describes surgical tools having an end effector operatively coupled to an elongate shaft and, more specifically, surgical tools and end effectors that are capable of both placing sutures and severing surgical thread during a surgical procedure.

Unwanted or premature severance of surgical thread during a suturing operation can be problematic. The present disclosure describes surgical tools and end effectors that are configured to perform multiple aspects of a suturing operation and methods for use thereof, but with a significantly lower risk of premature surgical thread severance. More specifically, the present disclosure describes surgical tools and end effectors incorporating both a needle driver and a bladed cutting instrument, in which the blades are obscured until needed for severing surgical thread. As such, the surgical tools and end effectors disclosed herein are much less susceptible to inadvertent or premature surgical thread severance during a suturing operation.

Before discussing additional details of the surgical tools and end effectors of the present disclosure and methods for their use, a brief overview of laparoscopic and similar surgical tools and robotic surgical systems will be provided hereinafter in order for the embodiments of the present disclosure to be better understood.

The terms "proximal" and "distal" are defined herein relative to the location of engagement by a surgeon or a robotic manipulator. The term "proximal" refers to a position closer to the location of engagement (i.e., further away from a patient), and the term "distal" refers to a position more removed from the location of engagement (i.e., nearer to a patient). Moreover, directional terms such as above, below, upper, lower, upward, downward, left, right, and the like are used to describe relative position in the figures and thus should not be considered limiting.

Figure 1:
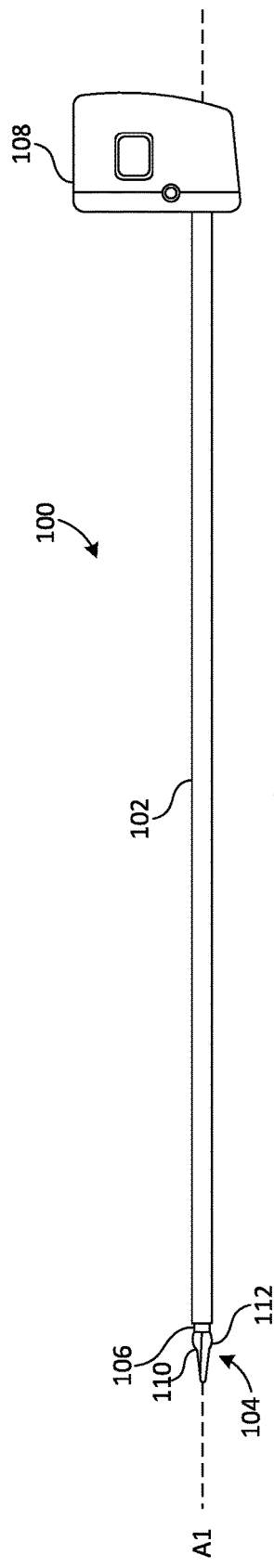
FIG. 1 shows a diagram of an illustrative surgical tool that may incorporate certain principles of the present disclosure.

FIG. 1 shows a diagram of an illustrative surgical tool 100 that may incorporate certain principles of the present disclosure. Surgical tool 100 includes elongate shaft 102, end effector 104 located at a distal end of elongate shaft 102, and housing 108 located at a proximal end of elongate shaft 102. Wrist 106 is also located at a distal end of elongate shaft 102 and couples end effector 104 thereto. Housing 108 may be configured for releasable coupling with a mounting fixture of a robotic manipulator, alternately referred to as a "robot" or "surgical robot." Housing 108 contains various mechanisms (obscured in FIG. 1) which may be actuated to produce one or more resultant motions in end effector 104. More particularly, actuation within housing 108 controls the operation of end effector 104 via retraction and extension of cables or similar elongate members (obscured in FIG. 1) that are operably engaged with end effector 104.

Housing 108 may be releasably coupled with the mounting fixture of a robotic manipulator in a variety of ways, such as by clamping or clipping thereto, or slidably mating therewith. Illustrative mechanisms for releasably coupling housing 108 to a mounting fixture are described in more detail in U.S. Patent Application Publications 2015/0209965 and 2015/0025549, incorporated herein by reference in their entirety, and U.S. patent application Ser. No. 15/200,283, filed on Jul. 1, 2016 and entitled "Methods, Systems, And Devices For Initializing A Surgical Tool," which is also incorporated herein by reference in its entirety. Illustrative robotic surgical systems are also described in these references as well as in U.S. Pat. No. 8,831,782, which is also incorporated herein by reference in its entirety.

Continuing with FIG. 1, end effector 104 is configured to move relative to elongate shaft 102 at wrist 106, such as by pivoting at wrist 106, to position end effector 104 at a desired orientation and location relative to a surgical site during a surgical procedure. Housing 108 includes various components designed to position and operate various features of end effector 104 (e.g., one or more of clamping, firing, rotation, articulation, energy delivery, and the like). In illustrative embodiments, one or more elongate members extend from housing 108 through wrist 106 to facilitate articulation of end effector 104, as discussed in more detail herein. In at least some embodiments, elongate shaft 102 and end effector 104 coupled distally thereto are configured to rotate about longitudinal axis A1. In some embodiments, various components of housing 108 can be configured to facilitate rotational motion of elongate shaft 102 and end effector 104 about longitudinal axis A1. In other embodiments, elongate shaft 102 may be fixed to housing 108, in which case surgical tool 100 may be rotated by the robotic manipulator to reposition elongate shaft 102 and end effector 104.

Surgical tool 100, particularly at end effector 104, can be configured to perform at least one surgical function. The choice of end effector 104 can determine which surgical function surgical tool 100 is able to perform. Illustrative configurations of end effector 104 that may be present in surgical tool 100 include, for example, forceps, graspers, needle drivers, scissors, electrocauterization tools that apply energy to tissue, staplers, clip appliers, suctioning tools, irrigation tools, imaging devices (e.g., endoscopes or ultrasonic probes), and any combination thereof. In at least one embodiment, surgical tool 100 may be configured to apply mechanical force to a tissue. The mechanical force can be conveyed to end effector 104 via the cables or similar elongate members extending through elongate shaft 102.

Elongate shaft 102 extends distally from housing 108 and has at least one lumen (see FIG. 3) extending internally therethrough. Elongate shaft 102 may be affixed to housing 108, but alternately may be releasably coupled so as to be interchangeable with other types of elongate shafts, such as elongate shafts have a differing diameter. In at least some embodiments, elongate shaft 102 may be rotatably coupled to housing 108.

End effector 104 can have a variety of sizes, shapes and configurations. In the illustrative configuration of FIG. 1, end effector 104 comprises a tissue grasper or needle driver having opposing jaws 110 and 112 that are configured to move (pivot) relative to one another between open and closed positions. In addition, the entirety of end effector 104 may pivot relative to elongate shaft 102 at wrist 106. Pivoting may place end effector 104 in a desired position to engage tissue or another surface during a surgical procedure.

Wrist 106 can likewise have a variety of configurations. In the illustrative configuration of FIG. 1, wrist 106 includes a joint configured to allow movement of end effector 104 relative to elongate shaft 102, such as a pivot joint at which jaws 110 and 112 are pivotally attached via a corresponding body. Illustrative configurations that may be similar to wrist 106 and are suitable for use in the embodiments of the present disclosure include those described in U.S. Patent Application Publications 2015/0209965 and 2015/0025549 and U.S. patent application Ser. No. 15/200,283, each previously incorporated by reference above.

Figure 2:
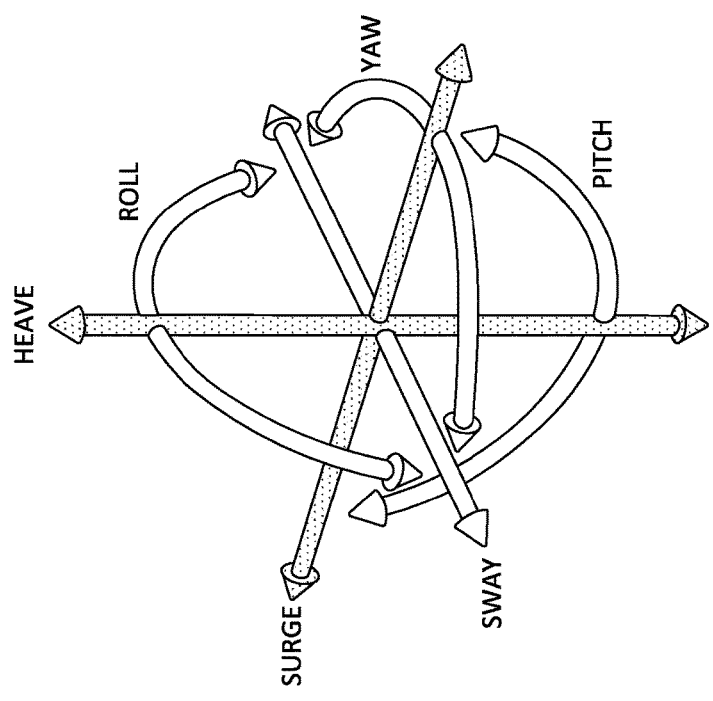
FIG. 2 shows a diagram illustrating the degrees of freedom through which a wrist of a surgical tool may articulate.

FIG. 2 shows a diagram illustrating the degrees of freedom through which wrist 106 may articulate. More specifically, the degrees of freedom available to wrist 106 are represented by three translational or position variables (e.g., surge, heave and sway) and three rotational or orientation variables (e.g., Euler angles or roll, pitch and yaw). The translational and rotational variables collectively describe the position and orientation of one or more components of a surgical system (e.g., wrist 106 and associated end effector 104) with respect to a given frame of reference, such as a Cartesian coordinate system or spherical coordinate system. As illustrated in FIG. 2, the term "surge" refers to forward and backward movement, the term "heave" refers to up and down movement, and the term "sway" refers to left and right movement. With regard to the rotational terms in FIG. 2, "roll" refers to side-to-side tilting, "pitch" refers to forward and backward tilting, and "yaw" refers to left and right turning.

In some embodiments, a pivoting motion can include pitch movement about a first axis of wrist 106 (e.g., X-axis), yaw movement about a second axis of wrist 106 (e.g., Y-axis), and combinations thereof to allow for 360° rotational movement of end effector 104 about wrist 106. In other embodiments, a pivoting motion can be limited to movement in a single plane such that end effector 104 rotates only in a single plane (e.g., only pitch movement about a first axis of wrist 106 or only yaw movement about a second axis of wrist 106).

Surgical tool 100 includes a plurality of cables or similar elongate members (obscured in FIG. 1), which are configured to impart movement to end effector 104 relative to elongate shaft 102. Illustrative forms of the elongate members include, for example, cables, bands, lines, cords, wires, ropes, strings, twisted strings and the like. Elongate members can be formed from any of a variety of high-durability materials, such as a metal (e.g., tungsten, stainless steel, and like materials) or a polymer. In at least one embodiment, one or more of the elongate members may be made of a flexible material. Illustrative cables and similar elongate members are described in U.S. Patent Application Publications 2015/0209965 and 2015/0025549, each previously incorporated herein by reference.

Figure 3:
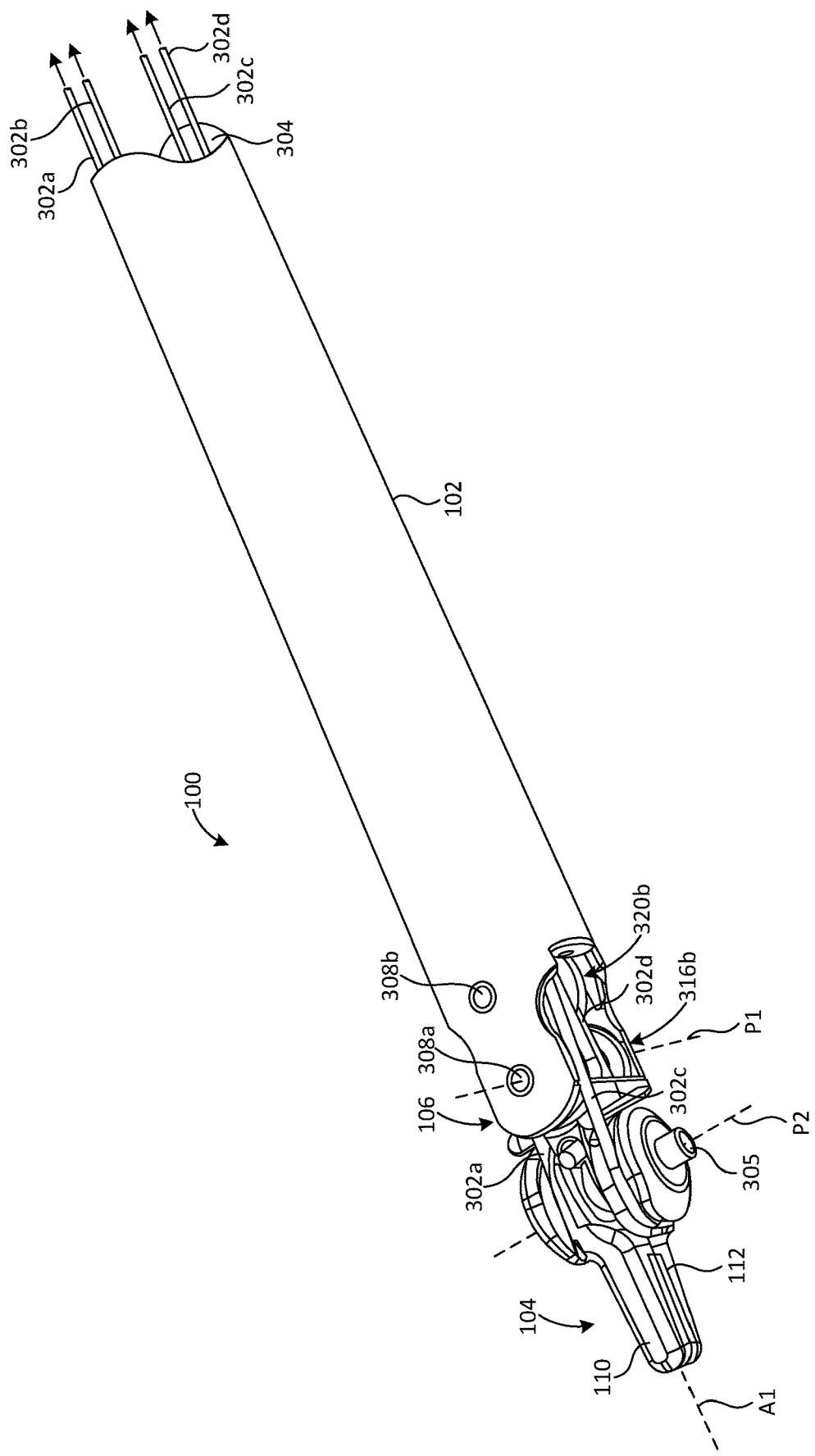
FIGS. 3-5 show various views of an illustrative surgical tool containing an end effector.
Figure 4:
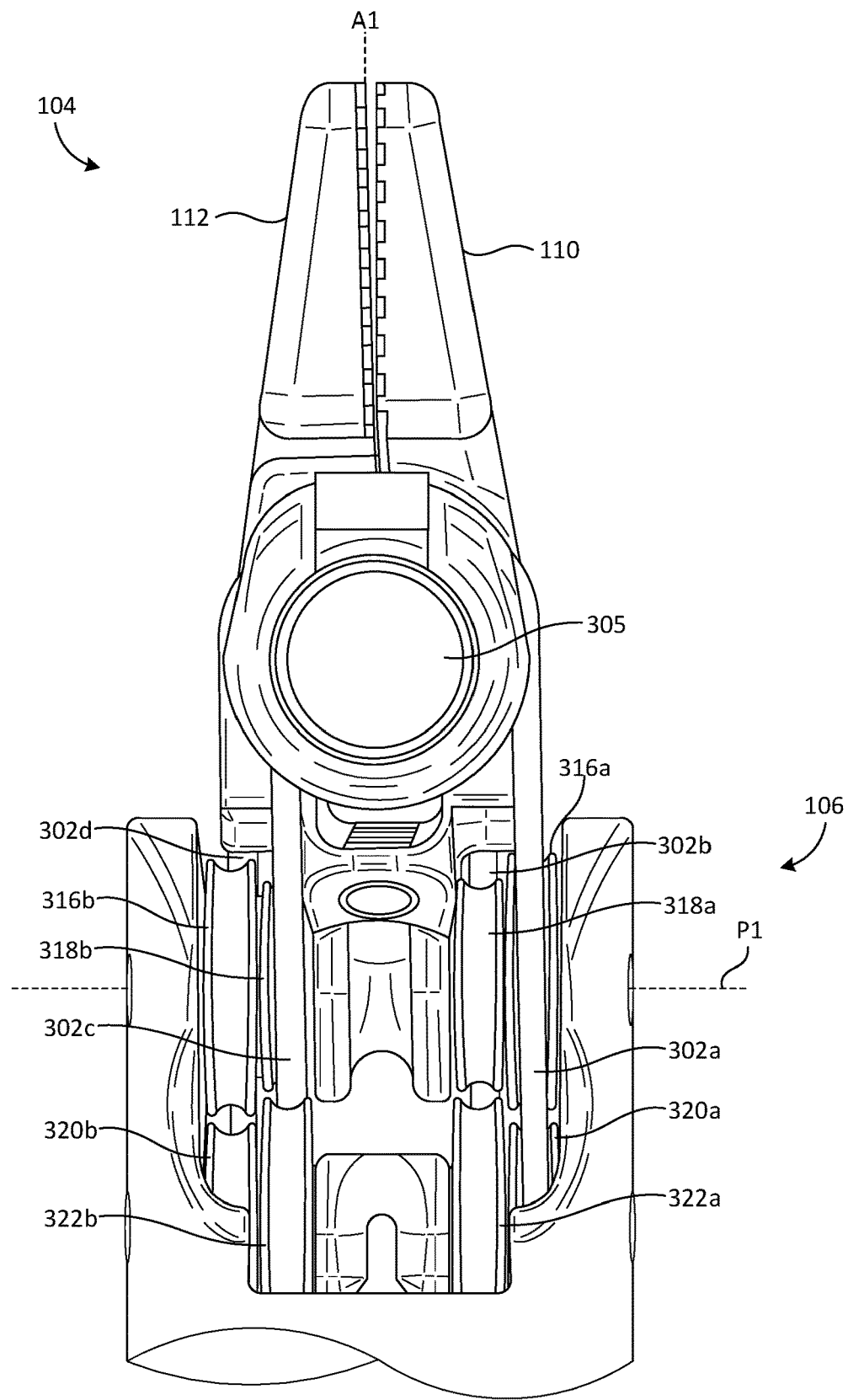
Figure 5:
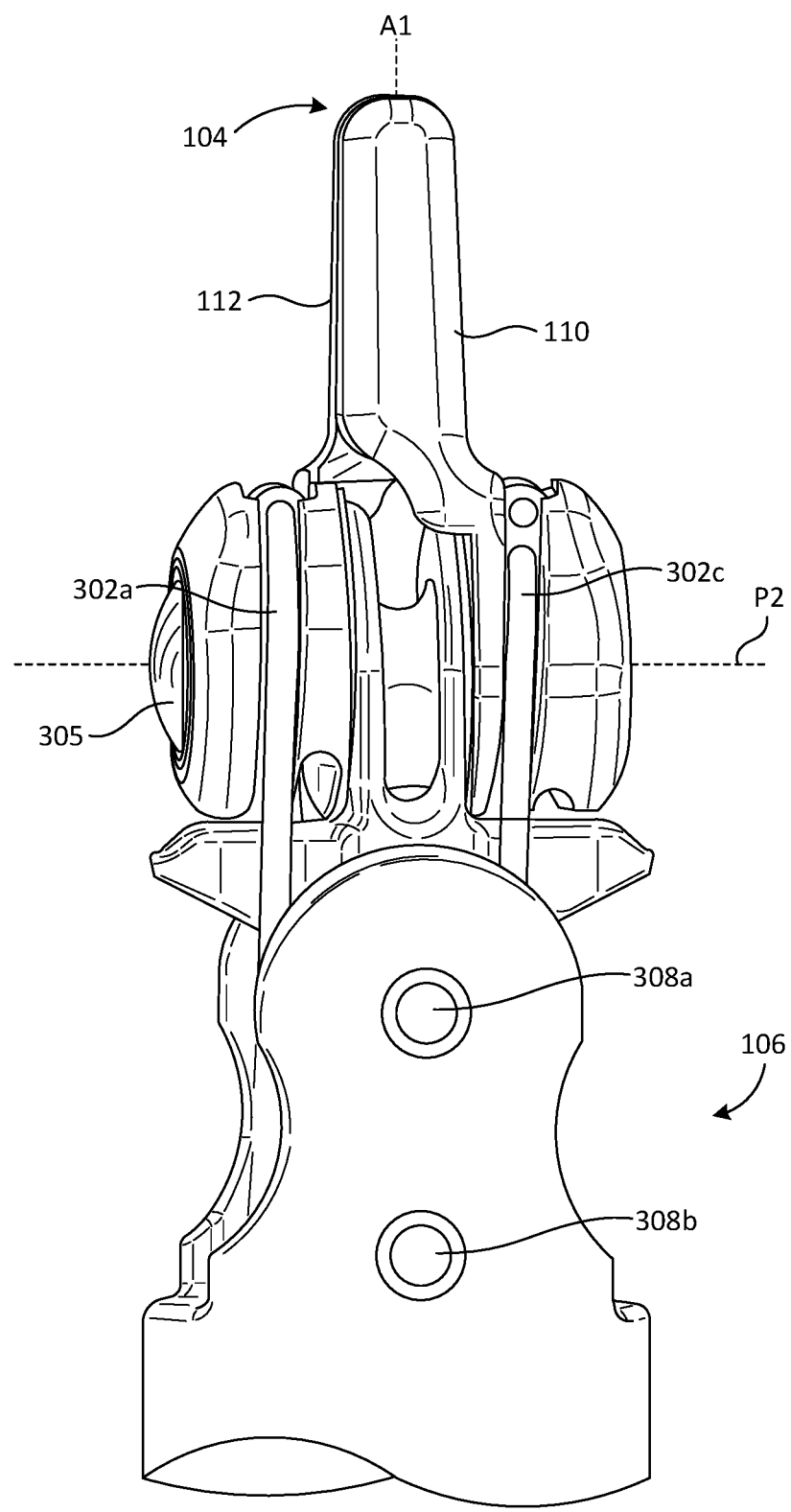

The disposition of the elongate members within surgical tool 100 is illustrated more fully in FIGS. 3-5, which show various enlarged views of elongate shaft 102, end effector 104, and wrist 106. Although surgical tool 100 is depicted as including four elongate members 302a-d, one pair being operatively coupled to each of jaws 110 and 112, alternative configurations can have differing numbers of elongate members. For example, a surgical tool having an end effector that does not require internal motion can include two elongate members configured to provide articulation upon longitudinal tensioning and de-tensioning.

As shown in FIGS. 3-5, elongate members 302a-d extend longitudinally within lumen 304 of elongate shaft 102 through wrist 106 and operably engage end effector 104, as described hereinafter. The proximal ends of elongate members 302a-d are similarly operably engaged with components in housing 108 (not shown in FIGS. 3-5). One or more of elongate members 302a-d may be selectively translated longitudinally to cause end effector 104 to move (e.g., pivot in one or more locations) relative to elongate shaft 102. Depending on the required motion, one or more of elongate members 302a-d may translate longitudinally to articulate end effector 104 (e.g., to move jaws 110 and 112 at an angle in a same direction), to open end effector 104 (e.g., to move jaws 110 and 112 away from one another), to close end effector 104 (e.g., to move jaws 110 and 112 toward one other), or any combination thereof.

Although a single lumen 304 is depicted in FIG. 3, multiple lumens can be present in alternative embodiments, such that one or more of elongate members 302a-d is housed within each of the multiple lumens. In further alternative embodiments, one or more of elongate members 302a-d can extend along the exterior of elongate shaft 102, such as in longitudinal channels formed in an exterior surface of elongate shaft 102.

Referring still to FIG. 3, and with further reference to FIGS. 4 and 5, wrist 106 includes multiple pulleys for engaging and redirecting elongate members 302a-d during their longitudinal translation. Specifically, wrist 106 includes distal plurality of pulleys 316a, 316b, 318a and 318b, and proximal plurality of pulleys 320a, 320b, 322a and 322b. Clearance (best shown in FIG. 4) is provided between corresponding pulleys in the distal and proximal pluralities of pulleys, which is sized for passage of elongate members 302a-d therethrough. Pulleys 316a, 316b, 318a and 318b are mounted to distal wrist axle 308a, and pulleys 320a, 320b, 322a and 322b are mounted to proximal wrist axle 308b. End effector 104 is operably coupled to wrist 106 such that distal wrist axle 308a defines first pivot axis P1 during operation thereof.

Surgical tool 100 further includes second pivot axis P2 along end effector axle 305, about which jaws 110 and 112 are configured to pivot relative to each other from a closed position through a range of open positions, and/or about which jaws 110 and 112 are configured to move together during articulation of end effector 104. As illustrated, second pivot axis P2 is substantially perpendicular to longitudinal axis A1. A person having ordinary skill in the art will appreciate that axes A1 and P2 may not be precisely perpendicular to one another but nevertheless be considered to be substantially perpendicular due to any number of factors, such as manufacturing tolerance and precision of measurement devices.

Surgical tool 100 has two joints at second pivot axis P2, one joint for each of jaws 110 and 112. Actuation of at least one of elongate members 302a-d causes movement of jaw 110 and/or jaw 112 at the associated joint(s) along second pivot axis P2. In an exemplary embodiment, jaws 110 and 112 are configured to pivot in tandem at their associated joints. That is, during opening of jaws 110 and 112, each of jaws 110 and 112 rotates at its associated joint, and during closing of jaws 110 and 112, each of jaws 110 and 112 rotates in the opposite direction at its associated joint.

Figure 6:
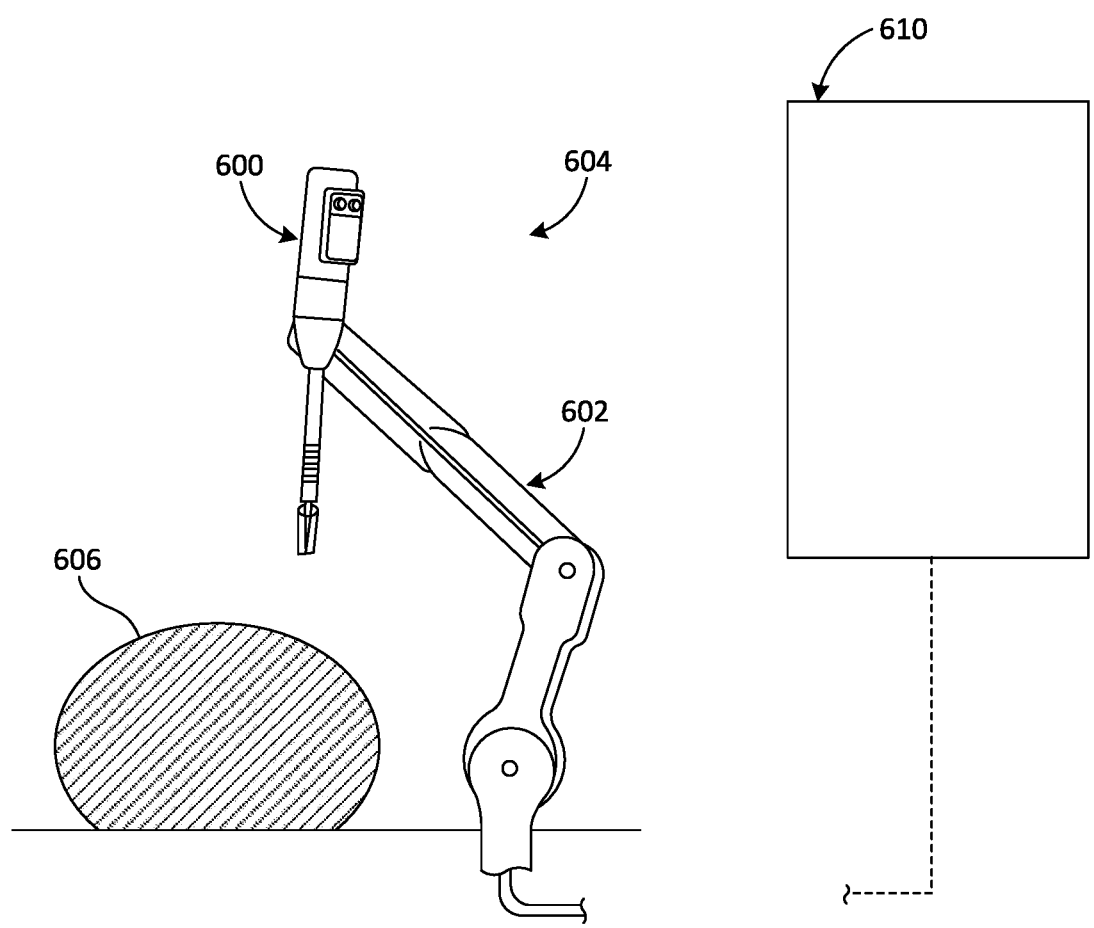
FIG. 6 shows a diagram illustrating coupling between a surgical tool and a robotic manipulator.

In at least some embodiments, surgical tool 100 is configured for releasable coupling to a robotic manipulator. FIG. 6 shows a diagram illustrating coupling between a surgical tool and a robotic manipulator. It is to be understood that the manner of coupling depicted in FIG. 6 is illustrative in nature so that certain embodiments of the present disclosure can be better understood. In non-limiting variations, the type of surgical tool and/or robotic manipulator, and/or the manner of coupling, for example, may differ based upon considerations that will be familiar to one having ordinary skill in the art.

As depicted in FIG. 6, surgical tool 600 is coupled to arm 602 of robotic manipulator 604. Robotic manipulator 604 and surgical tool 600 are positioned adjacent to patient 606 in order to conduct a surgical procedure thereon. Robotic manipulator 604 is in electronic communication with control system 610, through which a surgeon may move arm 602 and/or actuate surgical tool 600 according to one or more embodiments. Although FIG. 6 has depicted a wired connection between surgical tool 600 and control system 610, wireless configurations also reside within the scope of the present disclosure. In one or more embodiments, control system 610 may include vision control, processing control, or any combination thereof, using any combination of software and hardware implementation.

As discussed previously, surgical tools conventionally configured both to manipulate a needle during a suturing operation and to sever surgical thread upon completion of the suturing operation can be problematic due to incidental interaction between the surgical thread and a bladed cutting instrument of the surgical tool. Accordingly, the present disclosure provides end effectors for a surgical tool that are capable of grasping and releasing a needle (or possibly tissue) during suturing and subsequently severing surgical thread upon completing a surgical procedure, but with a much lower risk of premature thread severance. More specifically, the end effectors described herein incorporate both a needle driver and bladed cutting instrument, where the blades of the bladed cutting instrument are positioned for cutting by engaging one another only when severance of surgical thread is desired. The blade configuration within the end effectors disclosed herein advantageously offers a lower incidence of premature surgical thread severance compared to otherwise comparably equipped conventional dual-function end effectors.

The end effectors described herein advantageously incorporate both needle-driving and thread-severing capabilities within the footprint of a single end effector, thus providing compatibility with other types of laparoscopic and robotic surgical equipment and procedures. More specifically, the end effectors described herein include opposing jaws capable of opening and closing to grasp and release tissue, surgical thread, needles, and the like. As described in further detail herein, the opposing jaws can be further manipulated by opening beyond a predetermined angle to expose blades for cutting surgical thread when desired, such as upon the completion of suturing. Specifically, the opposing jaws can be opened beyond a predetermined angle sufficient to expose blades located proximal to a pivot joint of the opposing jaws upon the needle driver. The blades are then ready to receive and sever surgical thread upon at least partially closing the jaws. As such, the end effectors of the present disclosure can facilitate multiple aspects of a suturing operation, particularly needle grasping/releasing and surgical thread severance.

The end effectors described herein are configured such that cutting surfaces of the blades are not engaged against one another or with another surface until severance of surgical thread is desired. More specifically, from a fully closed jaw position up to the predetermined angle, the blades overlap and provide no aperture (gap) into which surgical thread can be received. As such, the blades are effectively occluded, except when severance of surgical thread is desired. By keeping the blades non-engaged until severing of the surgical thread is desired, friction is reduced and the risk of accidental cutting considerably decreases. Further advantages of the end effectors and surgical tools of the present disclosure are provided hereinbelow.

Figure 7:
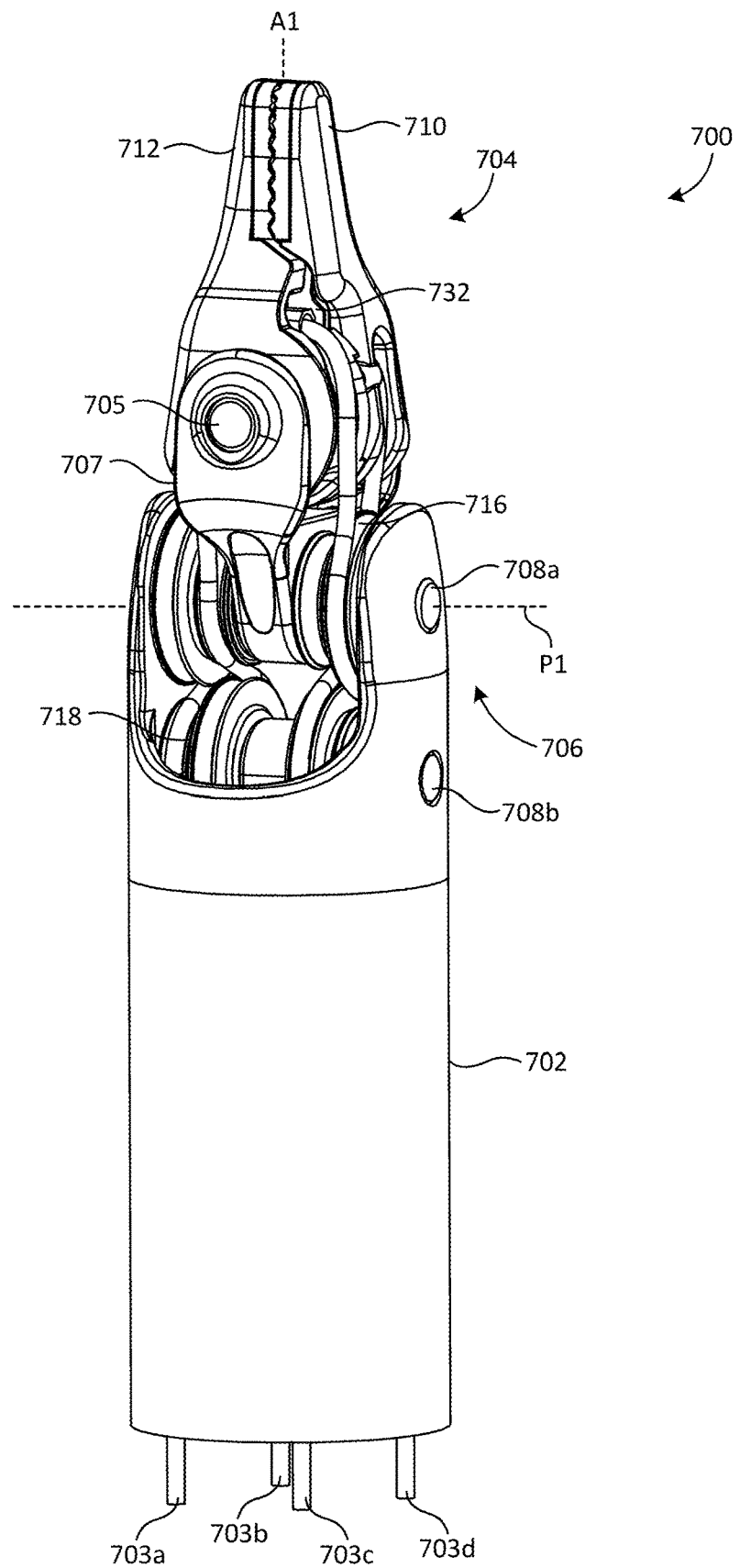
FIGS. 7-9 show various isometric views at various operational stages of an illustrative surgical tool incorporating a needle driver and a bladed cutting instrument within an end effector.
Figure 8:
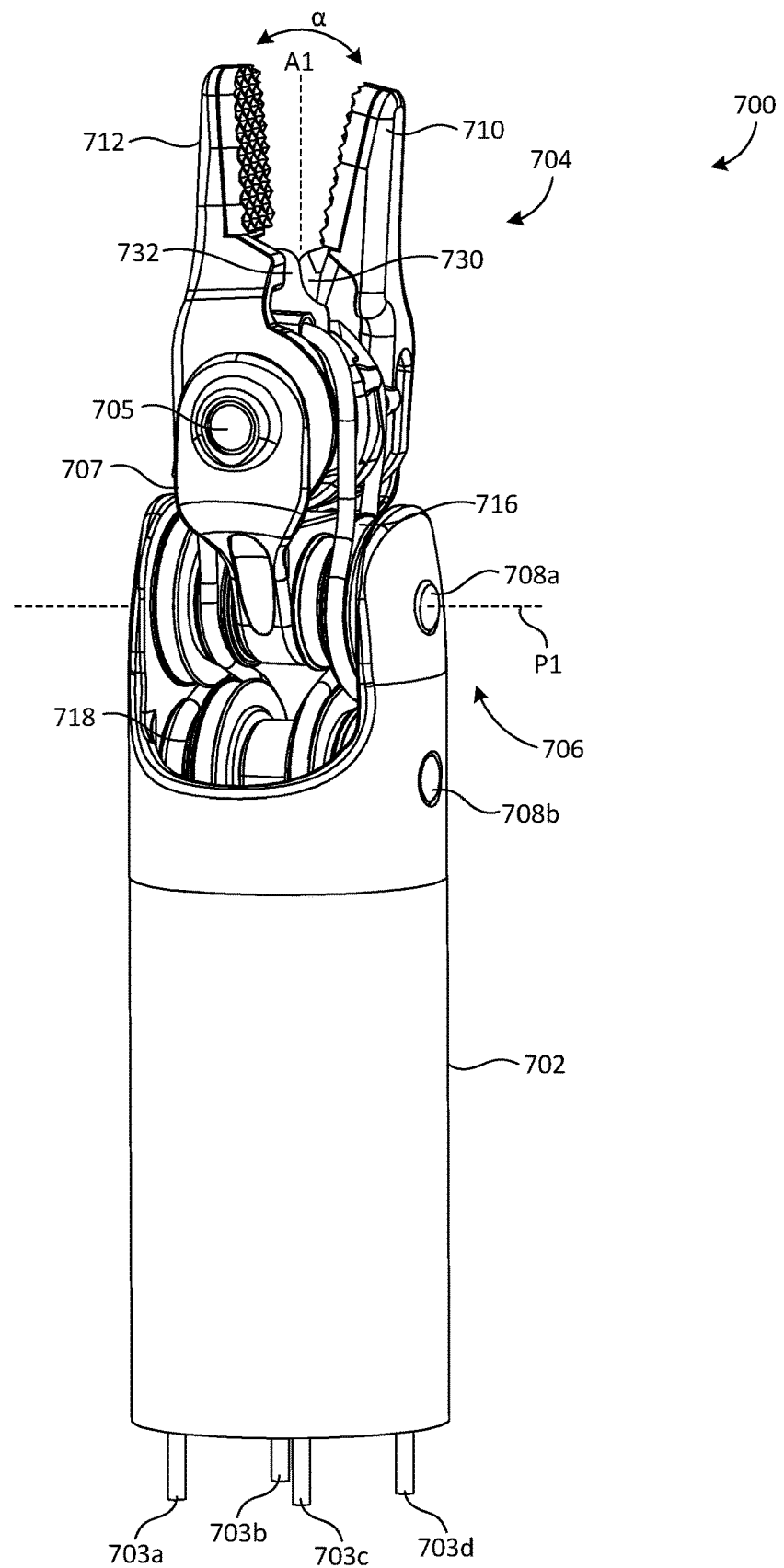
Figure 9:
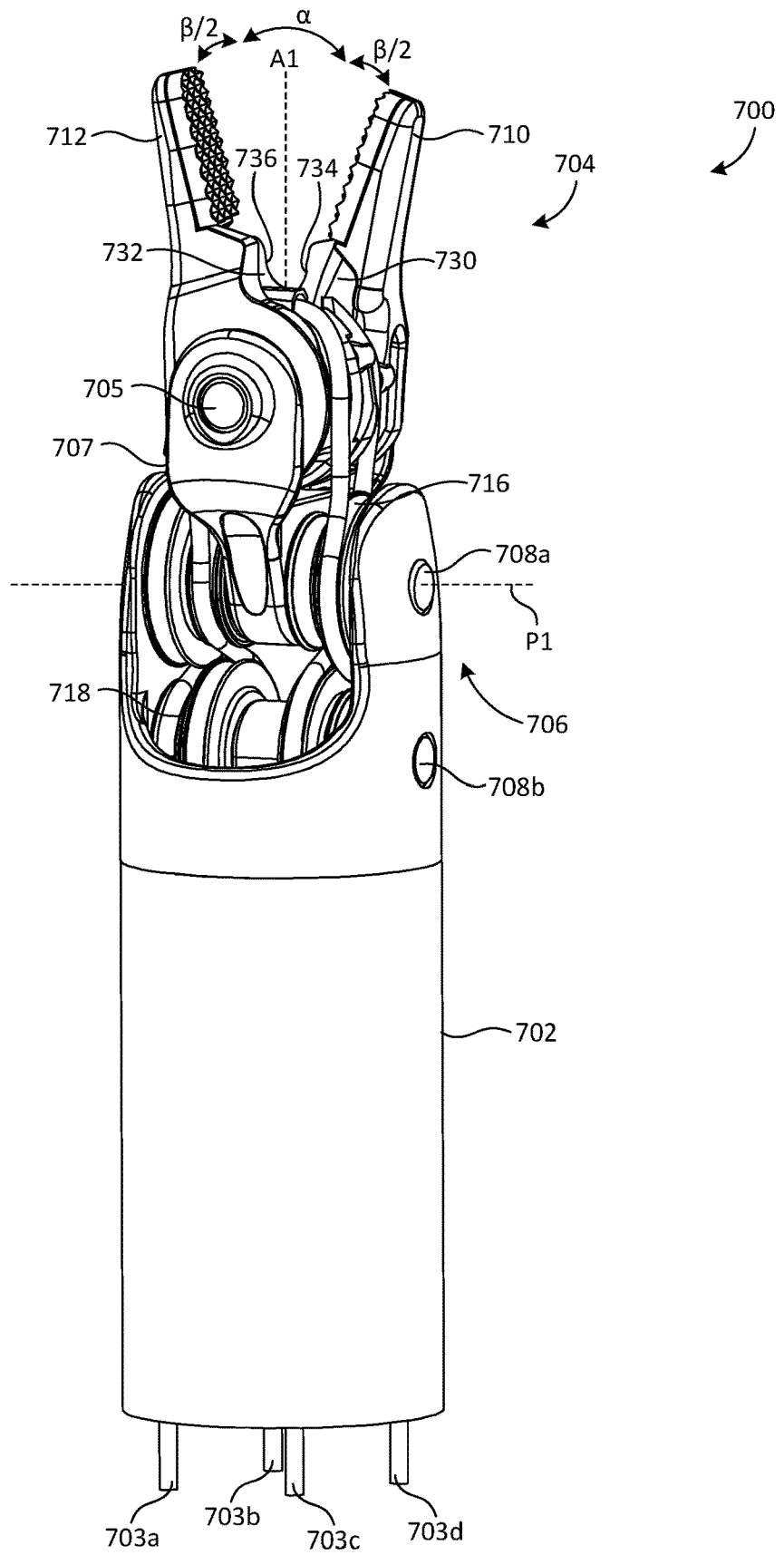

FIGS. 7-9 show isometric views of illustrative surgical tool 700 at various operational stages. Surgical tool 700 contains end effector 704 that incorporates a needle driver and cutting blades. As shown, end effector 704 is operably coupled to wrist 706 via distal clevis 707, which is pivotally engaged with distal wrist axle 708a. Distal plurality of pulleys 716 are also mounted to distal wrist axle 708a, and proximal plurality of pulleys 718 are mounted to proximal wrist axle 708b. Elongate members 703a-d extend longitudinally within elongate shaft 702 and pass through proximal and distal pluralities of pulleys 716 and 718 before engaging end effector 704. Axes A1 and P1 are the same as those defined with respect to FIGS. 1 and 3-5.

Jaws 710 and 712 of end effector 704 are configured to pivot with respect to one another via rotation about end effector axle 705, which is operably coupled to distal clevis 707. FIG. 7 shows jaws 710 and 712 in a fully closed configuration, FIG. 8 shows jaws 710 and 712 in a partially open configuration, and FIG. 9 shows jaws 710 and 712 in a fully open configuration. Jaws 710 and 712 are capable of pivoting between the fully closed and fully open configurations, as well as to any degree in between. Consequently, the depicted configurations should not be considered limiting.

End effector 704 is configured to grasp a needle (or possibly tissue) during a suturing operation when jaws 710 and 712 are closed and to release the needle (or possibly tissue) when jaws 710 and 712 are at least partially open. The extent of opening needed to release a needle during suturing need not necessarily be as wide as that depicted in FIGS. 8 and 9. The closed configuration of FIG. 7 and the partially open configuration of FIG. 8 represent the typical pivoting extremes of jaws 710 and 712 when severing of surgical thread is not desired (i.e., when grasping and releasing a needle). In practice, a much more limited opening of jaws 710 and 712 than that depicted in FIG. 8 can be employed when releasing a needle during a suturing operation, and it can be advantageous to limit the range of opening, as discussed hereinafter.

As shown in FIG. 9, end effector 704 further includes a bladed cutting instrument with opposing cutting surfaces that include cutting bodies 730 and 732. Cutting body 730 includes blade 734, and cutting body 732 includes blade 736. As described hereinafter, blades 734 and 736 are substantially exposed only when jaws 710 and 712 are opened beyond a predetermined angle. When exposed, gap 721 is formed between blades 734 and 736 to receive surgical thread for cutting. When jaws 710 and 712 are positioned at an angle less than the predetermined angle, gap 721 is closed and blades 734 and 736 can no longer accept additional surgical thread for cutting. As such, the risk of premature thread severance is significantly reduced.

In illustrative embodiments, jaws 710 and 712 of end effector 704 may pivot through a first range of angles (α) without exposing or bringing blades 734 and 736 into engagement with one another (see FIG. 8). First range of angles (α) represents the angular positions through which jaws 710 and 712 may pivot between a closed configuration and a partially opened configuration. In illustrative embodiments, jaws 710 and 712 may be articulated within a first range of angles (α) residing between 0 degrees and about 40 degrees, or between about 0 degrees and about 30 degrees, or between 0 degrees and about 25 degrees without exposing or bringing blades 734 and 736 into engagement with one another, where an angle of 0 degrees represents a configuration in which jaws 710 and 712 are fully closed. As such, in some embodiments, jaws 710 and 712 may each be articulated through an angular range of α/2 without exposing gap 721 between blades 734 and 736. Cutting bodies 730 and 732 may come into slidable engagement with one another at the same angle at which blades 734 and 736 come into engagement with one another. In other embodiments, cutting bodies 730 and 732 may come into slidable engagement with one another at an angle smaller than that at which blades 734 and 736 come into engagement with one another. For example, in some embodiments, cutting bodies 730 and 732 may come into slidable engagement at an angular value of (α) ranging between about 10 and about 15 degrees, or between about 15 and about 20 degrees, or between about 20 degrees and about 25 degrees, at which point blades 734 and 736 remain non-engaged with one another.

In further illustrative embodiments, jaws 710 and 712 may be articulated through a second range of angles (β) to open gap 721 between blades 734 and 736 (see FIG. 9). That is, second range of angles (β) corresponds to the additional angular translation required to move from sliding engagement between blades 734 and 736 to form gap 721 in between. In illustrative embodiments, gap 721 may be defined between blades 734 and 736 when jaws 710 and 712 are articulated within a second range of angles (β) residing between about 25 degrees and about 45 degrees, or between about 30 degrees and about 45 degrees, or between about 25 degrees and about 40 degrees, or between 30 degrees and about 40 degrees, where 0 degrees represents a configuration in which jaws 710 and 712 are fully closed against one another. As will be appreciated, the second range of angles (β) includes angles greater than those in the first range of angles (α).

In various embodiments, the first range of angles (α) represents the extent of jaw articulation over which surgical tool 700 is typically utilized for performing a suturing operation, with an angle of substantially 0 degrees being employed when grasping a suturing needle and an angle up to about 25 degrees, or up to about 30 degrees, or up to about 40 degrees being employed when the suturing needle is released. In more particular operational embodiments, the suturing needle may be released from jaws 710 and 712 at an angle much less than that at which gap 721 becomes defined, such as any angle above 0 degrees and up to about 20 degrees, or any angle above 0 degrees and up to about 15 degrees. In still more specific embodiments, jaws 710 and 712 may be articulated through a range of angles such that the suturing needle is released before cutting bodies 730 and 732 come into slidable engagement with one another. Releasing the suturing needle without cutting bodies 730 and 732 coming into slidable engagement with one another can be desirable for minimizing friction during operation of surgical tool 700. Likewise, the second range of angles (β) corresponds to the extent of jaw articulation over which surgical tool 700 is capable of receiving surgical thread for severing by placing the surgical thread in gap 721 defined between blades 734 and 736 and then decreasing the angular separation until blades 734 and 736 slidingly engage one another once again.

When jaws 710 and 712 are closed, cutting bodies 730 and 732 are not engaged with one another (see FIG. 17B) and blades 734 and 736 are occluded, as described in more detail below. At some point between the closed configuration of FIG. 7 and the partially opened configuration of FIG. 8, cutting bodies 730 and 732 come into sliding engagement with one another, and in the configuration of FIG. 8, blades 734 and 736 slidingly engage one another. A portion of cutting bodies 730 and 732 remain in sliding engagement with one another upon further pivoting to the fully opened configuration of FIG. 9.

In some embodiments, cutting body(ies) 730 and/or 732 may be fabricated integrally as a one-piece construct with a jaw body rotatably coupling corresponding jaw(s) 710 and/or 712 to end effector axle 705, thereby allowing articulation to take place. In other embodiments, cutting body(ies) 730 and/or 732 and a corresponding jaw body may be fabricated as separate components that are configured to mate together so that they can pivot in tandem with one another.

Figure 10:
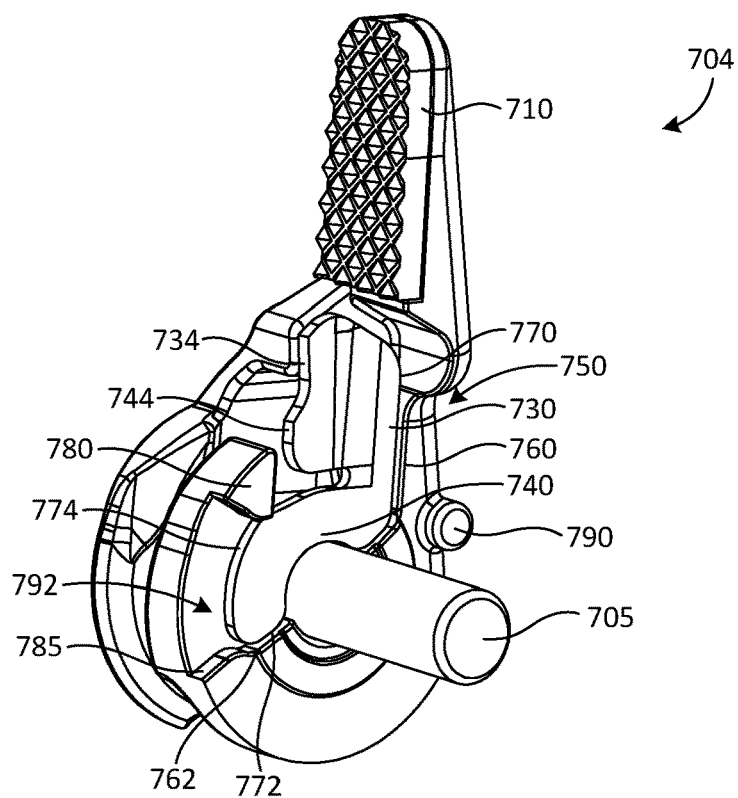
FIGS. 10-12 show isometric views of a portion of an end effector incorporating a bladed cutting instrument.
Figure 11:
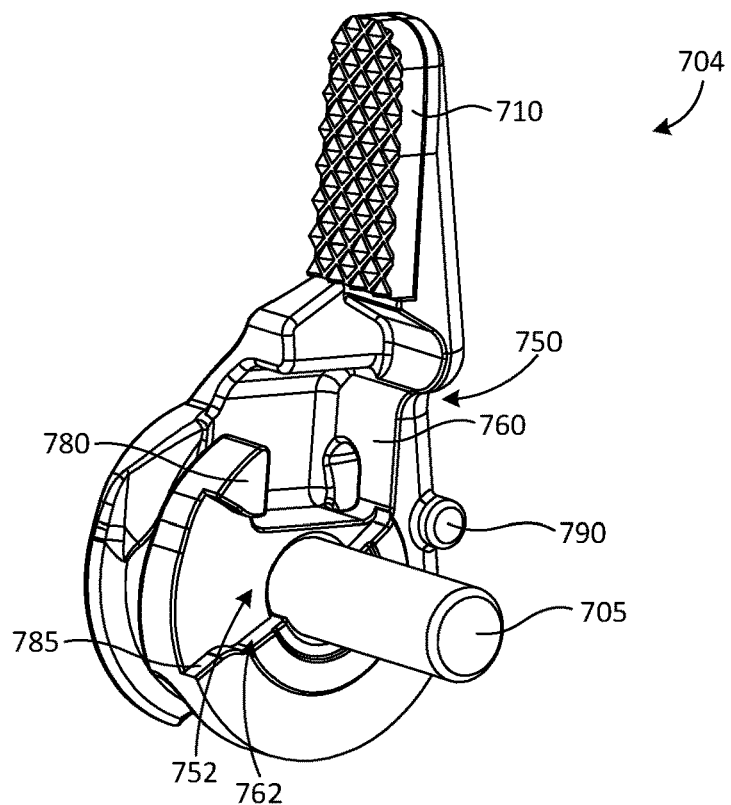

FIGS. 10 and 11 show isometric views of a portion of end effector 704. More particularly, FIG. 10 shows jaw 710 and associated cutting body 730 mounted to end effector axis 705, and FIG. 11 shows jaw 710 alone without cutting body 730 present to enable viewing of the internal features of jaw body 750. Jaw 712 and cutting body 732 are also omitted from FIGS. 10 and 11 to enable viewing of the internal features of jaw body 750. It is to be understood that jaw 710 is representative of jaw 712, and the discussion of jaw 710 and its relationship to cutting body 730 is equally applicable to jaw 712 and cutting body 732.

As illustrated, jaw body 750 defines a recess 752 or a similar type of internal pocket (best seen in FIG. 11). Recess 752 is sized to receive and seat cutting body 730. Cutting body 730 includes blade 734 extending from wing 744. Leg 740 also extends from cutting body 730 and, as illustrated, engages end effector axle 705, which helps rotatably mount cutting body 730 thereto. Although leg 740 is shown as only partially encircling end effector axle 705, it is to be recognized that it may circumferentially surround end effector axle 705 in alternative embodiments and still allow rotational engagement to be realized.

When properly mounted in recess 752, cutting body 730 moves in tandem with jaw 710. More specifically, recess 752 includes first surface 760 and second surface 762, each configured to engage cutting body 730 during operation. When jaw 710 and corresponding jaw body 750 are rotated counterclockwise, first surface 760 engages edge 770 of cutting body 730 and urges similar counterclockwise rotation of cutting body 730 about end effector axle 705. During clockwise rotation, second surface 762 engages edge 772 provided on leg 740 and promotes similar clockwise rotation of cutting body 730 about end effector axle 705. In some embodiments, tab 780 may extend into recess 752 to engage edge 774 of cutting body 730, which further promotes retention of cutting body 730 within recess 752 during rotation in either direction.

In some embodiments, cutting body 730 may be secured within recess 752 to prevent inadvertent separation of the two components. Suitable technique for securing cutting body 730 may include, for example, staking, welding, soldering, adhesive bonding, mechanical entrapment, snap fitting, press fitting, interference fitting, swage fitting, lock washers, fasteners, and the like. According to some embodiments, cutting body 730, for instance, may be secured within recess 752 by welding, brazing, or adhesive bonding. In other embodiments, cutting body 730 may be mechanically fastened within recess 752, such as by using one or more mechanical fasteners (e.g., screws, bolts, pins, and the like). In yet other embodiments, cutting body 730 may be secured within recess 752 via an interference or shrink fit. If cutting body 730 is fixedly coupled to jaw body 750 within recess 752 (e.g., by welding, brazing, adhesive bonding, mechanical fasteners, and the like), edges 770, 772 and/or 774 need not necessarily engage corresponding first surface 760, second surface 762 and/or tab 780 within jaw body 750 in order to promote in-tandem pivoting with jaw 710.

Figure 12:
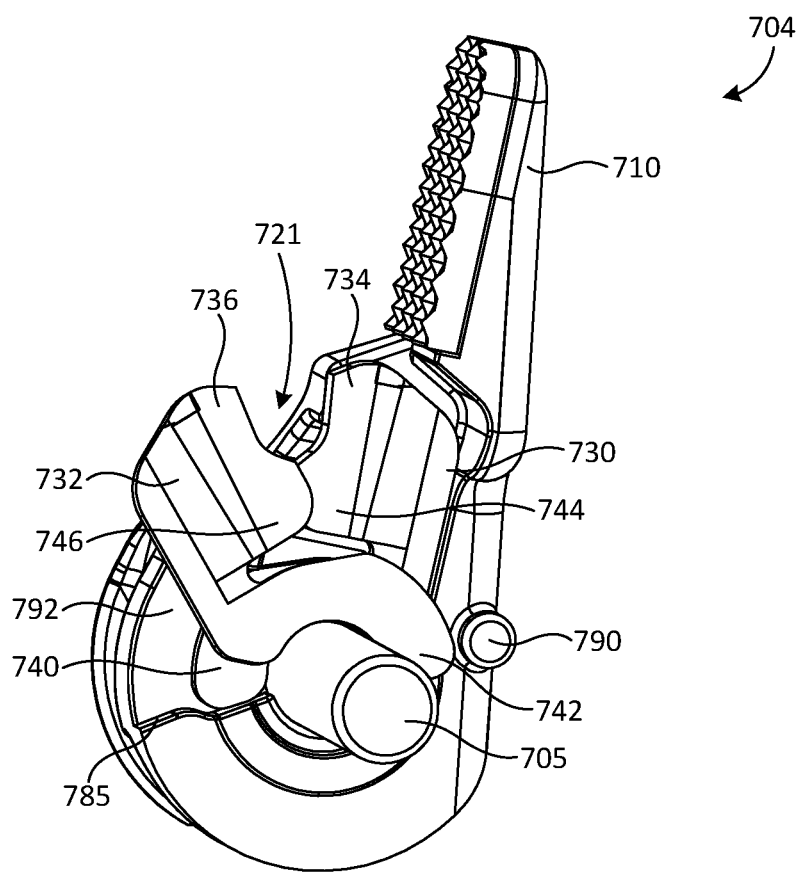

FIG. 12 is another isometric view of a portion of end effector 704, now showing both cutting bodies 730 and 732 in the fully opened configuration. Jaw 712 is again omitted to enable viewing of cutting bodies 730 and 732 and their interoperability. Similar to cutting body 730, cutting body 732 includes blade 736 extending from wing 746 and leg 742 engaging end effector axle 705. Similar to cutting body 730, cutting body 732 is also configured to be received and seated within a recess or internal pocket associated with a jaw body of jaw 712.

Legs 740 and 742 of cutting bodies 730 and 732 are laterally offset (i.e., spaced apart) from one another along the length of end effector axle 705, and they remain laterally offset throughout the full range of articulation of jaws 710 and 712. In contrast, wings 744 and 746 are biased toward each other such that a portion of wings 744 and 746 enjoy a mutual sliding engagement, even when jaws 710 and 712 are in the fully opened configuration. If jaws 710 and 712 were permitted to open past the fully opened configuration depicted in FIG. 9 (i.e., past a predetermined angular limit, such as discussed above), wings 744 and 746 would eventually disengage from one another and lead to edge abutment thereof, thereby preventing jaws 710 and 712 from re-closing.

To prevent jaws 710 and 712 from opening past the predetermined angular limit, jaw body 750 may further include hard stop 790. While not shown in FIG. 12, the jaw body of corresponding jaw 712 may also include a similar hard stop. Hard stops 790 may be configured to limit the extent to which jaws 710 and 712 may pivot. More specifically, hard stop 790 of jaw body 750 may be configured to engage a feature upon the jaw body of jaw 712 and preclude further jaw articulation. Similarly, the hard stop provided on the jaw body of jaw 712 may be configured to engage a feature upon jaw body 750 of jaw 710 (e.g., end shoulder 785) to prevent further jaw articulation.

Each hard stop 790 is positioned to move within groove 792 defined upon opposing jaw body 750 as jaws 710 and 712 progress through their full range of motion. In particular, groove 792 is defined between tab 780, end shoulder 785 and an edge of leg 740. Groove 792 upon jaw body 750 is configured to limit movement of hard stop 790 located upon the jaw body of jaw 712, while a corresponding groove (not shown) defined upon jaw 712 is configured to limit movement of hard stop 790 located upon jaw body 750 of jaw 710. Each groove 792 includes end shoulder 785 designed to limit the range of motion and prevent jaws 710 and 712 from opening past a predetermined angular limit. More specifically, end shoulder 785 is configured to engage hard stop 790 to prevent further opening of jaws 710 and 712.

Figure 13:
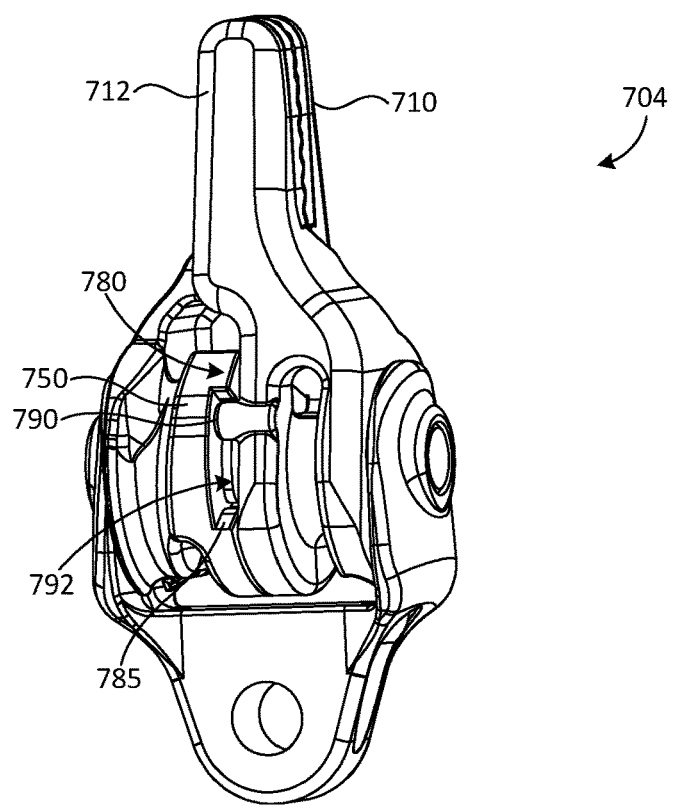
FIGS. 13 and 14 show isometric views of a portion of an end effector incorporating a bladed cutting instrument, in which a hard stop limits the range of motion.
Figure 14:
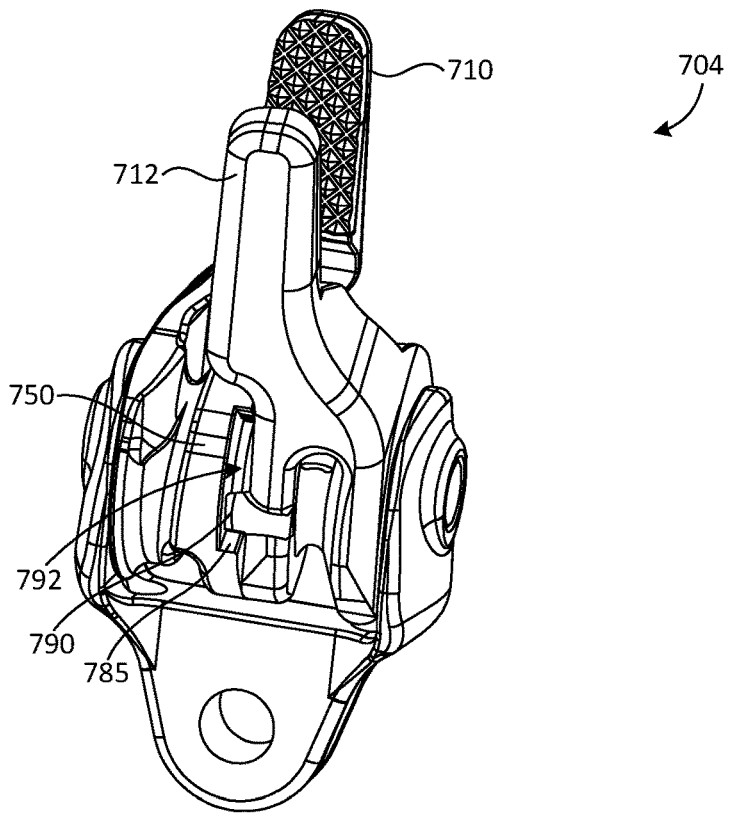

FIGS. 13 and 14 are isometric views of end effector 704 as hard stop 790 moves between the fully closed configuration (FIG. 13) and the fully opened configuration (FIG. 14). As illustrated, hard stop 790 upon the jaw body of jaw 712 is visible and positioned for movement within groove 792 defined upon jaw body 750 of jaw 710. Although not shown, a corresponding hard stop associated with jaw 710 is similarly located for movement within a groove defined on the jaw body of jaw 712 on the opposing side of end effector 704.

As shown in FIG. 14, hard stop 790 engages end shoulder 785 when jaw 712 is fully opened. Further opening of jaw 712 is precluded by the engagement between end shoulder 785 and hard stop 790. Similar limiting of the movement of jaw 710 may also be provided by the hard stop located upon jaw body 750 of jaw 710. In contrast, when jaw 712 is closed, as in FIG. 13, hard stop 790 engages tab 780 defined upon jaw body 750 of jaw 710. Although FIG. 13 shows engagement between tab 780 and hard stop 790 when jaw 712 is closed, it is to be recognized that engagement need not necessarily occur upon closing jaw 712. In particular, once closed, jaw 712 can proceed no further and there is no express need for hard stop 790 to engage tab 780 to preclude further closure. When jaw 712 is partially opened, as depicted in FIG. 8 or in a position intermediate between FIGS. 7 and 8, hard stop 790 is located at a position within groove 792 between tab 780 and end shoulder 785.

Further details of the sliding engagement between cutting bodies 730 and 732 is provided in FIGS. 15A, 15B, 16A, 16B, 17A and 17B. Jaws 710 and 712 are omitted in these FIGS. to enable better depiction of the interoperability of cutting bodies 730 and 732.

Figure 15A:
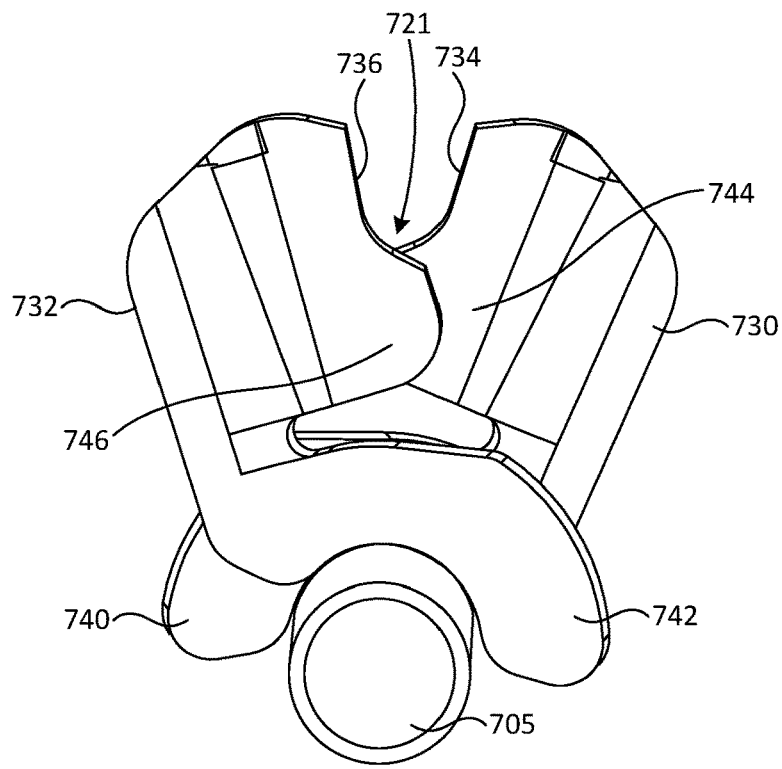
FIGS. 15A, 15B, 16A, 16B, 17A and 17B show top and side views at various operational stages of cutting bodies within an illustrative end effector.
Figure 15B:
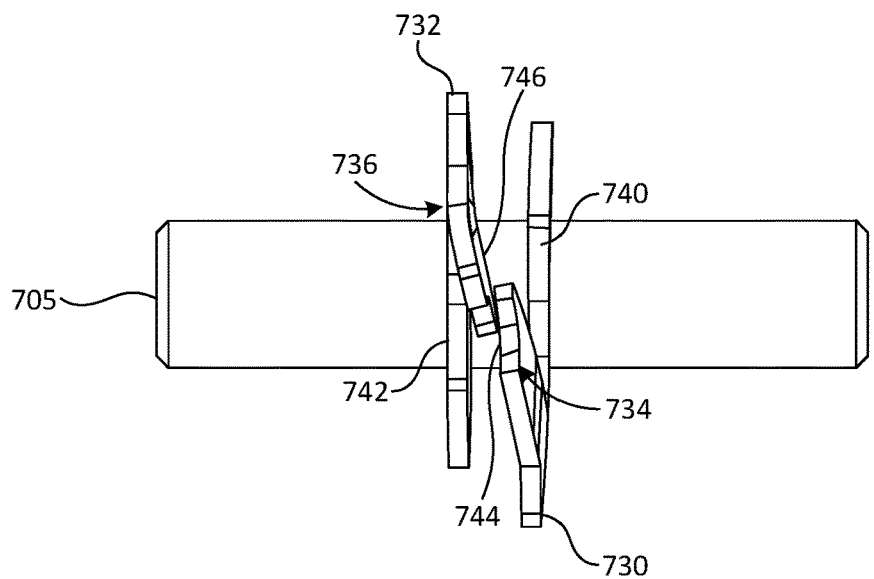

FIGS. 15A and 15B show side and top views, respectively, of cutting bodies 730 and 732 mounted to end effector axle 705 when jaws 710 and 712 (not shown) are in a fully opened configuration (corresponding to FIG. 9). As illustrated, blades 734 and 736 of cutting bodies 730 and 732, respectively, are angularly separated from each other to define gap 721. As discussed above, cutting bodies 730 and 732 are configured to rotate with respect to end effector axle 705 and in-tandem with the rotation of corresponding jaws 710 and 712, respectively, such that blades 734 and 736 can be brought into angular sliding engagement with one another.

As best seen in FIG. 15B, wings 744 and 746 extend from blades 734 and 736, respectively, and are angled (tapered) toward one another. Because of the angled (tapered) configuration of each wing 744 and 746, a portion of each wing 744 and 746 remains slidably engaged with the opposing wing 744 and 746 when end effector 704 is in the fully opened configuration, even when blades 734 and 736 are angularly spaced apart. As such, wings 744 and 746 exert a force against one another (i.e., are forcibly engaged) in the depicted fully opened configuration. With wings 744 and 746 being tapered inwardly and engaging one another in at least some configurations, legs 740 and 742 remain spaced apart along end effector axle 705.

In some embodiments, a biasing element may be employed to maintain wings 744 and 746 in forcible engagement with one another. In some embodiments, suitable biasing elements may include shims, washers or similar spacers, any of which may also employ springs or be configured as springs. For example, in some embodiments, a Belleville washer may be a suitable biasing element. More specifically, in some embodiments, one or more biasing elements may be placed longitudinally upon end effector axle 705 to position legs 740 and 742 closer together to one another. The one or more biasing elements may be located between wing 740 and jaw body 750, and/or one or more biasing elements may likewise be placed between wing 742 and its corresponding jaw body. When positioned in this manner the one or more biasing elements may urge wings 744 and 746 into more effective engagement with one another.

In some or other embodiments, a compression spring may be used as a suitable biasing element. One or more compression springs may be positioned longitudinally upon end effector axle 705 similarly to the other types of biasing elements discussed previously, and the one or more compression springs may function comparably to urge wings 744 and 746 into more effective engagement with one another. Moreover, in some embodiments, compression springs and the other types of biasing elements may be used in combination with one another to produce a suitable biasing force.

Figure 16A:
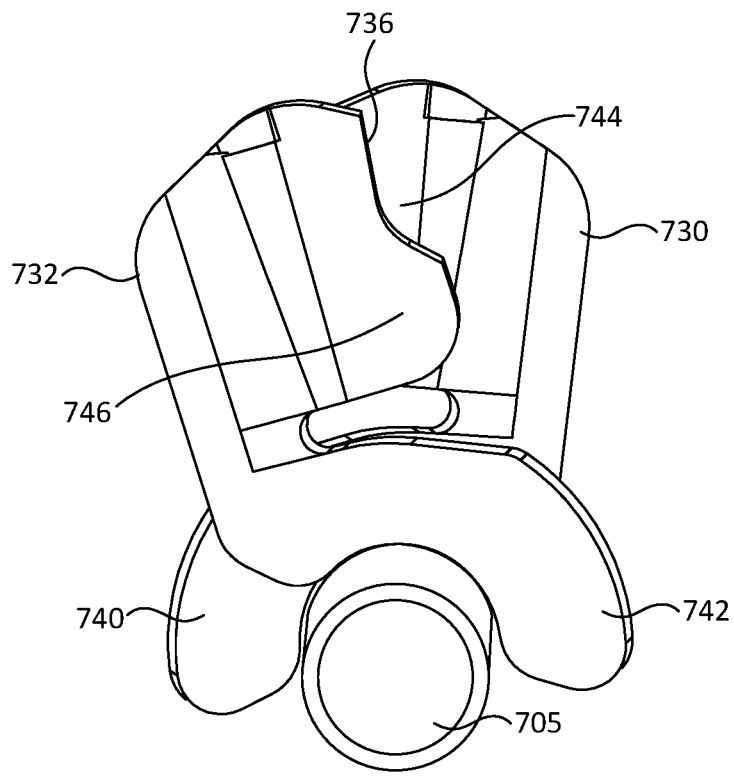
Figure 16B:
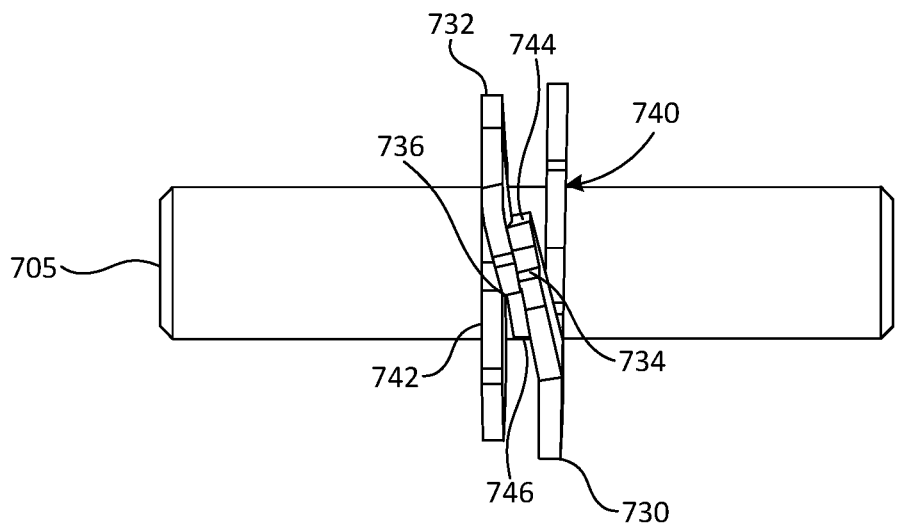

FIGS. 16A and 16B show side and top views, respectively, of cutting bodies 730 and 732 mounted to end effector axle 705, but with jaws 710 and 712 (not shown) moved to a partially opened configuration (corresponding to FIG. 8). As jaws 710 and 712 pivot from the fully opened configuration of FIGS. 15A and 15B to the partially opened configuration of FIGS. 16A and 16B, cutting bodies 730 and 732 continue to slidingly engage one another as gap 721 between cutting bodies 730 and 732 closes. As gap 721 closes, blades 734 and 736 are progressively brought into lateral engagement, which facilitates cutting of objects (e.g., surgical thread) placed within gap 721 prior to closure thereof. Accordingly, blades 734 and 736 operate similarly to standard scissors or shearing devices.

In the partially opened configuration of FIGS. 16A and 16B, wing 744 continues to slidably engage a portion of cutting body 732, and wing 746 likewise continues to slidably engage a portion of cutting body 730 while blades 734 and 736 are laterally engaged with one another. Once gap 721 has closed and blades 734 and 736 are laterally engaged, blades 734 and 736 are effectively obscured and unable to receive and/or sever additional surgical thread accidentally during a suturing operation. Advantageously, the forced lateral engagement between wings 744 and 746 allows very fine surgical thread to be severed.

Figure 17A:
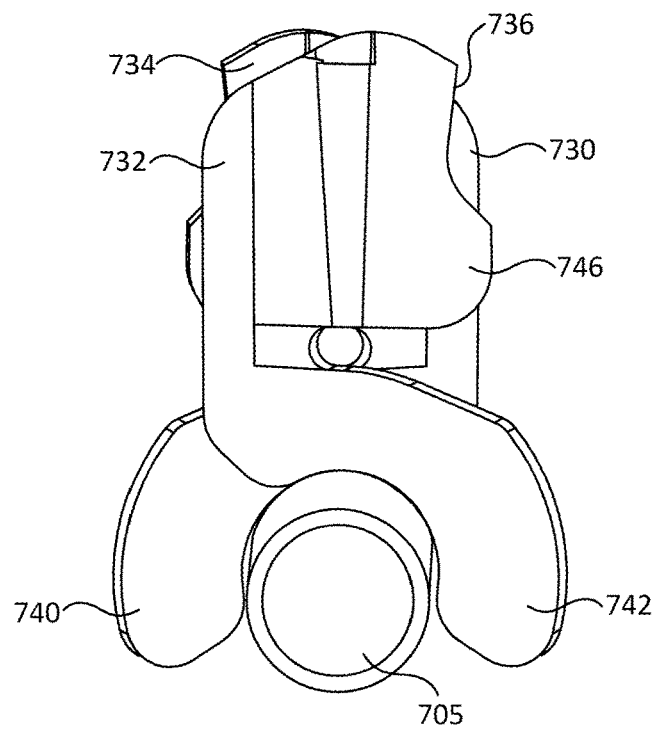
Figure 17B:
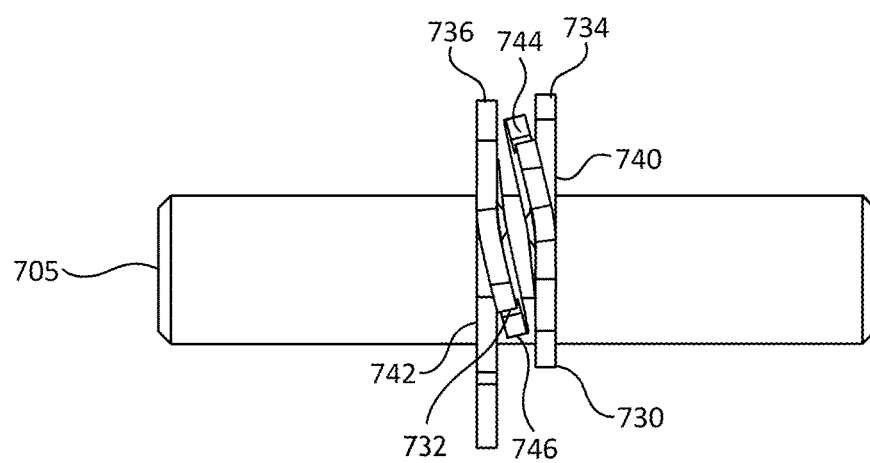

FIGS. 17A and 17B show side and top views, respectively, of cutting bodies 730 and 732 mounted to end effector axle 705, but with the jaws 710 and 712 (not shown) moved to a closed configuration (corresponding to FIG. 7). Continued closing of jaws 710 and 712 moves blades 734 and 736 angularly past one another. As jaws 710 and 712 further close, blades 734 and 736 remain obscured such that they are unable to receive and/or sever surgical thread accidentally. At some point after blades 734 and 736 angularly traverse one another, wings 744 and 746 also disengage from one another, as best shown in FIG. 17B. The angled (tapered) configuration of wings 744 and 746 may be such that disengagement of wings 744 and 746 occurs immediately after blades 734 and 736 angularly traverse one another. Alternatively, cutting bodies 730 and 732 may remain slidingly engaged for some time before becoming disengaged prior to or upon full closing of end effector 704. Angles at which engagement and disengagement occur are discussed above.

By maintaining wings 744 and 746 disengaged from one another when cutting of surgical thread is unnecessary, less friction is encountered when closing and partially opening jaws 710 and 712 to grasp and release a needle (or possibly tissue) during a suturing operation than would otherwise be encountered were wings 744 and 746 to remain in continuous sliding engagement. As such, easier tool operation is provided by bringing wings 744 and 746 into sliding engagement, and thereby increasing friction, only when severing of surgical thread is desired.

As will be appreciated, the operations outlined above in FIGS. 15A, 15B, 16A, 16B, 17A and 17B are fully reversible to reopen end effector 704 to the fully open configuration. More specifically, reversing the pivoting direction of jaws 710 and 712 causes a corresponding reversal in the sliding engagement of cutting bodies 730 and 732 and corresponding wings 744 and 746. When jaws 710 and 712 are fully closed (e.g., FIG. 7), such as when grasping a needle during a suturing operation, cutting bodies 730 and 732 are fully disengaged from one another (see FIGS. 17A and 17B). As jaws 710 and 712 partially open, cutting bodies 730 and 732 again become slidably engaged at wings 744 and 746 before blades 734 and 736 angularly align and engage one another (see FIGS. 16A and 16B). Unlike the disengagement that may occur upon opening jaws 710 and 712 too widely (i.e., beyond a predetermined angle), cutting bodies 730 and 732 are able to readily re-engage one another from a closed configuration due to the forced engagement between the two. Continued pivoting of jaws 710 and 712 to the fully opened configuration (e.g., FIG. 9) maintains cutting bodies 730 and 732 in sliding engagement with one another at wings 744 and 746, and progressively exposes gap 721 between blades 734 and 736 to allow receipt and severance of surgical thread.

Although wings 744 and 746 may become slidingly engaged when releasing a needle during a suturing operation, jaws 710 and 712 may alternately be opened to a lesser extent to release the needle while still maintaining wings 744 and 746 disengaged from one another. That is, needle release from end effector 704 may take place with jaws 710 and 712 in a configuration intermediate between that of FIGS. 7 and 8. Suitable angles for needle release are provided hereinabove. Operating surgical tool 700 in this manner allows friction to be maintained at a low level during suturing and increased once severing of surgical thread is desired.

Materials suitable for forming cutting bodies 730 and 732 are not considered to be particularly limited, other than being biocompatible. In illustrative embodiments, suitable materials for cutting bodies 730 and 732 may include, for example, metals (e.g., stainless steel) or ceramics. In some embodiments, sufficiently hard polymeric materials may also be suitable. In some embodiments, jaws 710 and 712 and cutting bodies 730 and 732 may be formed from the same class of material, such as a stainless steel. In other embodiments, jaws 710 and 712 and cutting bodies 730 and 732 may be formed from entirely different materials. In more particular embodiments, cutting bodies 730 and 732 may be formed from 301¾ hard stainless steel, and jaws 710 and 712 may be formed from 17-4 PH full hard stainless steel or similar stainless steel.

Accordingly, the present disclosure also provides methods for using the above-described surgical tools and similar surgical tools during a suturing operation. In various embodiments, the methods may comprise grasping a needle having surgical thread attached thereto with an end effector of a surgical tool, the end effector comprising first and second jaws and first and second cutting bodies that are configured to move (pivot) in tandem with one another. The opposing jaws are in a closed configuration and the cutting bodies are disengaged from one another when grasping the needle. While grasping the needle, one or more sutures can be formed in a tissue using the surgical tool. Thereafter, the needle may be released by sufficiently opening the first and second jaws, in which case the first and second cutting bodies may or may not come into sliding engagement with one another. The first and second jaws may then be pivoted to a first open configuration in which the first and second cutting bodies and their associated blades come into sliding engagement with one another. When severing of the surgical thread is desired, the first and second jaws may be pivoted to a second open configuration to define a gap between the blades of the first and second cutting surfaces. A portion of the surgical thread is positioned in the gap, and the first and second jaws are closed to at least the first open configuration to sever the surgical thread. The first and second cutting surfaces remain slidably engaged with one another in the second open configuration and when returned to the first open configuration, as discussed herein.

As also discussed herein, opening and closing of the jaws in the above-described surgical tools may be promoted by tensioning and de-tensioning of one or more elongate members within an elongate shaft operably coupled to the end effector. In some embodiments, tensioning and de-tensioning of the elongate members within a first range of applied force may transition the end effector between the closed configuration and the first open configuration. In such embodiments, tensioning and de-tensioning of the elongate members within a second range of applied force may transition the end effector between the first open configuration and the second open configuration, where the second range of applied force is greater than the first range of applied force. That is, a "normal" range of applied force may be applied to operate the surgical tool when suturing, and a higher range of applied force can be utilized when the suturing operation is complete and severing of surgical thread is desired. In some or other embodiments, one or more first elongate members may deliver an applied force in the first range to transition the end effector between the closed configuration and the first open configuration, and one or more second elongate members may deliver an applied force in the second range to transition the end effector between the first open configuration and the second open configuration. The applied force in the second range may be greater than the applied force in the first range, according to some embodiments.

As such, a variety of controls may be provided to preclude opening of the end effector to the second open configuration other than at a desired time. During a suturing operation, the applied force may be maintained in the first range by any combination of software, hardware, engineering controls, or any combination thereof. For example, in some embodiments, a dedicated control (e.g., a foot pedal, special switch, voice command, or the like) may be utilized to apply a force in the second range to facilitate opening to the second open configuration. In some embodiments, the dedicated control is not utilized when transitioning the jaws of the end effector between the first open configuration and the closed configuration. In still other embodiments, the same controls may be utilized to transition the end effector between the closed configuration, the first open configuration and the second open configuration, and a surgeon may be provided with a heads up display, for example, or other output illustrating the extent to which the jaws of the end effector are opened.

Embodiments disclosed herein include:
A. Surgical tools. The surgical tools comprise: an elongate shaft having a proximal end and a distal end; and an end effector operably coupled to the elongate shaft at the distal end, the end effector comprising: an end effector axle; a first jaw and a second jaw rotatably mounted to the end effector axle; and a first cutting body having a first blade and second cutting body having a second blade, the first cutting body being configured to move in tandem with the first jaw and the second cutting body being configured to move in tandem with the second jaw; wherein the first and second jaws are movable between a closed configuration, in which the first and second jaws are positioned adjacent one another, a first open configuration, in which the first and second jaws are separated and the first and second blades remain occluded, and a second open configuration, in which the first and second blades are exposed and a gap is defined therebetween.
B. End effectors for surgical tool. The end effectors comprise: an end effector axle; a first jaw and a second jaw rotatably mounted to the end effector axle; and a first cutting body having a first blade and second cutting body having a second blade, the first cutting body being configured to move in tandem with the first jaw and the second cutting body being configured to move in tandem with the second jaw; wherein the first and second jaws are movable between a closed configuration, in which the first and second jaws are positioned adjacent one another, a first open configuration, in which the first and second jaws are separated and the first and second blades remain occluded, and a second open configuration, in which the first and second blades are exposed and a gap is defined therebetween.
C. Suturing methods. The methods comprise: grasping a needle having surgical thread attached thereto with an end effector of a surgical tool operably coupled to a distal end of an elongate shaft; wherein the end effector comprises an end effector axle, a first jaw and a second jaw rotatably mounted to the end effector axle, and a first cutting body having a first blade and second cutting body having a second blade, the first cutting body being configured to move in tandem with the first jaw and the second cutting body being configured to move in tandem with the second jaw; forming one or more sutures in a tissue with the needle and surgical thread; opening at least one of the first jaw and the second jaw sufficiently to release the needle, and then opening at least one of the first jaw and the second jaw to a first open configuration to bring the first and second cutting bodies into sliding engagement with one another; opening at least one of the first jaw and the second jaw to a second open configuration to define a gap between the first blade and the second blade, the second open configuration defining a larger angle between the first and second jaws than does the first open configuration; wherein the first and second cutting bodies remain in sliding engagement with one another in the second open configuration; positioning the surgical thread in the gap; and after positioning the surgical thread in the gap, partially closing at least one of the first jaw and the second jaw to the first open configuration to sever the surgical thread.

Each of embodiments A, B, and C may have one or more of the following additional elements in any combination Element 1: wherein the first cutting body includes a first leg that extends at least partially around the end effector axle, and the second cutting body includes a second leg that extends at least partially around the end effector axle and is laterally spaced from the first leg.

Element 2: wherein the first jaw contains a first recess configured to receive the first cutting body, and the second jaw contains a second recess configured to receive the second cutting body.

Element 3: wherein the first recess includes a first groove that terminates at a first end shoulder and the second recess includes a second groove that terminates at a second end shoulder, the end effector further comprising: a first hard stop provided on a jaw body of the first jaw; and a second hard stop provided on a jaw body of the second jaw; wherein the first hard stop is configured to move within the second groove and the second hard stop is configured to move within the first groove when the first and second jaws move between the closed configuration and the first and second open configurations.

Element 4: wherein the first cutting body comprises a first wing and the second cutting body comprises a second wing, and wherein the first and second wings are angled toward one another.

Element 5: wherein the first wing and the second wing are in sliding engagement when the gap is defined between the first blade and the second blade.

Element 6: wherein the first wing and the second wing are disengaged from one another when the first jaw and the second jaw are in the closed configuration.

Element 7: wherein the first open configuration is defined by an angular separation between the first and second jaws over a first range of angles ($\alpha$), and the second open configuration is defined by an angular separation between the first and second jaws over a second range of angles ($\beta$), the second range of angles being larger angles than the first range of angles.

Element 8: wherein the first and second blades are exposed and the gap is defined therebetween when the first and second jaws are angularly separated by about 25 degrees to about 40 degrees.

Element 9: wherein the first and second cutting bodies are in sliding engagement when the first and second jaws are in the second open configuration.

Element 10: wherein the first cutting body is operably engaged with a first recess defined in a jaw body of the first jaw, and the second cutting body is operably engaged with a second recess defined in a jaw body of the second jaw.

By way of non-limiting example, exemplary combinations applicable to A, B, and C include: the surgical tool of A or the end effector of B in combination with elements 1 and 2; 1, 2 and 3; 1 and 4, 1, 4 and 5, 1 and 4-6, 1 and 7; 1, 7 and 8; 1 and 8; 1 and 9; 2 and 3; 2 and 4; 2, 4 and 5; 2, 4 and 6; 2 and 7; 2, 7 and 8; 2 and 8; 2 and 9; 1 and 10; 3 and 10; 4 and 10; 4, 5 and 10; 4-6 and 10; 7 and 10; 8 and 10; 9 and 10; 3 and 4; 3 and 5, 3 and 6; 3 and 7; 3 and 8; 3 and 9; 4 and 5; 4 and 6; 4-6; 4 and 7; 4 and 8; 4 and 9; 7 and 8; 7 and 9; and 8 and 9; and the method of C in combination with elements 1 and 2; 1, 2 and 3; 1 and 4, 1, 4 and 5, 1 and 4-6, 1 and 7; 1, 7 and 8; 1 and 8; 2 and 3; 2 and 4; 2, 4 and 5; 2, 4 and 6; 2 and 7; 2, 7 and 8; 2 and 8; 1 and 10; 3 and 10; 4 and 10; 4, 5 and 10; 4-6 and 10; 7 and 10; 8 and 10; 3 and 4; 3 and 5, 3 and 6; 3 and 7; 3 and 8; 4 and 5; 4 and 6; 4-6; 4 and 7; 4 and 8; and 7 and 8.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A surgical tool, comprising:
   an elongate shaft; and
   an end effector operably coupled to a distal end of the elongate shaft and comprising:
   a first jaw with a first axis of rotation, a second jaw with a second axis of rotation, the first axis of rotation and second axis of rotation are rotatable about an end effector axle;
   a first blade that moves in tandem with the first jaw, the first blade having a third axis of rotation, a second blade that moves in tandem with the second jaw, the second blade having a fourth axis of rotation, the third axis of rotation and fourth axis of rotation are rotatably mounted to the end effector axel and laterally offset from the first and second axis of rotation,
   wherein the first and second jaws are movable between a closed configuration, in which the first and second jaws are positioned adjacent one another, a first open configuration, in which the first and second jaws are separated and the first and second blades remain occluded, and a second open configuration, in which the first and second blades are exposed and a gap is defined therebetween.

2. The surgical tool of claim 1, wherein the first blade and second blade have a non-linear cutting edge.

3. The surgical tool of claim 1, further comprising:
a first hard stop provided on the first jaw; and
a second hard stop provided on the second jaw.

4. The surgical tool of claim 1, wherein the first open configuration is defined by an angular separation between the first and second jaws over a first range of angles (α), and the second open configuration is defined by an angular separation between the first and second jaws over a second range of angles (β), the second range of angles being larger angles than the first range of angles.

5. The surgical tool of claim 1, wherein the first and second blades are exposed and the gap is defined therebetween when the first and second jaws are angularly separated by about 25 degrees to about 40 degrees.

6. An end effector comprising:
an end effector axle;
a first jaw with a first axis of rotation, a second jaw with a second axis of rotation, the first axis of rotation and second axis of rotation are rotatable about the end effector axle;
a first blade that moves in tandem with the first jaw, the first blade having a third axis of rotation, a second blade that moves in tandem with the second jaw, the second blade having a fourth axis of rotation, the third axis of rotation and fourth axis of rotation are rotatably mounted to the end effector axel and laterally offset from the first and second axis of rotation,
wherein the first and second jaws are movable between a closed configuration, in which the first and second jaws are positioned adjacent one another, a first open configuration, in which the first and second jaws are separated and the first and second blades remain occluded, and a second open configuration, in which the first and second blades are exposed and a gap is defined therebetween.

7. The end effector of claim 6, wherein the first blade and second blade have a non-linear cutting edge.

8. The end effector of claim 6, further comprising:
a first hard stop provided on the first jaw; and
a second hard stop provided on the second jaw.

9. The end effector of claim 6, wherein the first open configuration is defined by an angular separation between the first and second jaws over a first range of angles (α), and the second open configuration is defined by an angular separation between the first and second jaws over a second range of angles (β), the second range of angles being larger angles than the first range of angles.

10. The end effector of claim 6, wherein the first and second blades are exposed and the gap is defined therebetween when the first and second jaws are angularly separated by about 25 degrees to about 40 degrees.

11. A method, comprising:
grasping a needle having surgical thread attached thereto with an end effector of a surgical tool, the end effector including:
a first jaw with a first axis of rotation, a second jaw with a second axis of rotation, the first axis of rotation and second axis of rotation are rotatable about an end effector axle;
a first blade that moves in tandem with the first jaw, the first blade having a third axis of rotation, a second blade that moves in tandem with the second jaw, the second blade having a fourth axis of rotation, the third axis of rotation and fourth axis of rotation are rotatably mounted to the end effector axel and laterally offset from the first and second axis of rotation,
forming one or more sutures in tissue with the needle and surgical thread;
opening the first and second jaws from a closed configuration, to a first open configuration and thereby releasing the needle;
opening the first and second jaws to a second open configuration and thereby generating a gap between the first and second blades, the second open configuration defining a larger angle between the first and second jaws than the first open configuration;
positioning the surgical thread in the gap; and
moving the first and second jaws toward the first open configuration to sever the surgical thread.

* * * * *